United States Patent
Lai et al.

(10) Patent No.: US 6,306,842 B1
(45) Date of Patent: Oct. 23, 2001

(54) PROTECTED FORMS OF A COMBINATION OF PHARMACOLOGICALLY ACTIVE AGENTS AND USES THEREFOR

(75) Inventors: Ching-San Lai, Encinitas; Tingmin Wang, San Marcos, both of CA (US)

(73) Assignee: Medinox, Inc., San Diego, CA (US)

( * ) Notice: Subject to any disclaimer, the term of this patent is extended or adjusted under 35 U.S.C. 154(b) by 0 days.

(21) Appl. No.: 09/586,344

(22) Filed: Jun. 2, 2000

(51) Int. Cl.[7] .......................... A01N 37/36; A01N 43/00; A01N 51/00; A01N 37/10; A01N 37/18
(52) U.S. Cl. .......................... 514/159; 514/161; 514/569; 514/570; 514/567; 514/629; 514/158
(58) Field of Search ................................... 514/159, 161, 514/569, 570, 567, 158, 629

(56) References Cited

U.S. PATENT DOCUMENTS

| | | | |
|---|---|---|---|
| 5,603,959 | * | 2/1997 | Horrobin et al. . |
| 5,607,966 | * | 3/1997 | Hellberg et al. . |
| 6,025,353 | * | 2/2000 | Masferrer et al. . |

OTHER PUBLICATIONS

Bjarnason et al., "Side Effects of Nonsteroidal Anti–inflammatory Drugs on the Small and Large Intestine in Humans," *Gastroenterology*, 104:1832–1847, 1993.

Carson et al., "The Relative Gastrointestinal Toxicity of the Nonsteroidal Anti–inflammatory Drugs," *Arch. Intern. Med.*, 147:1054–1059, 1987.

Glaser et al., "Etodolac selectively inhibits human prostaglandin G/H synthase 2 (PGHS–2) versus human PGHS–1," *European Journal of Pharmacology*, 281:107–111, 1995.

Graham et al., "Nonsteroidal anti–inflammatory effect of sulindac sulfoxide and sulfide on gastric mucosa," *Clin. Pharmacol. Ther.*, 38:65–70, 1985.

Kaplan–Machlis and Klostermeyer, "The Cyclooxygenase–2 Inhibitors: Safety and Effectiveness," *The Annals of Pharmacotherapy*, 33:979–988, 1999.

Kargman et al., "Characterization of Prostaglandin G/H Synthase 1 and 2 in Rat, Dog, Monkey, and Human Gastrointestinal Tracts," *Gastroenterology*, 111:445–454, 1996.

Meade et al., "Differential Inhibition of Prostaglandin Endoperoxide Synthase (Cyclooxygenase) Isozymes by Aspirin and Other Non–steroidal Anti–inflammatory Drugs*," *The Journal of Biological Chemistry*, 268/9:6610–6614, 1993.

Mitchell et al., "Selectivity of nonsteroidal antiinflammatory drugs as inhibitors of constitutive and inducible cyclooxygenase," *Proc. Natl. Acad. Sci. USA*, 90:11693–11697, 1994.

Onoe et al., "IL–13 and IL–4 Inhibit Bone Resorption by Suppressing Cyclooxygenase–2–Dependent Prostaglandin Synthesis in Osteoblasts[1]," *The Journal of Immunology*, 156:758–764, 1996.

Slater et al., "Expression of cyclooxygenase types 1 and 2 in human fetal membranes at term," *Am. J. Obstet. Gynecol.*, 172:77–82, 1995.

Soll et al., "Nonsteroidal Anti–inflammatory Drugs and Peptic Ulcer Disease," *Annals of Internal Medicine*, 114:307–319, 1991.

John L. Wallace, "Nonsteroidal Anti–inflammatory Drugs and Gastroenteropathy: The Second Hundred Years," *Gastroenterology*, 112:1000–1016, 1997.

* cited by examiner

*Primary Examiner*—Paul J. Killos
*Assistant Examiner*—Mahreen Chaudhry
(74) *Attorney, Agent, or Firm*—Stephen E. Reiter; Foley & Lardner

(57) ABSTRACT

In accordance with the present invention, there are provided conjugates of a combination of pharmacologically active agents (e.g., NSAIDs and selective COX-2 inhibitors). Invention conjugates provide a new class of pharmacologically active agents (e.g., anti-inflammatory agents) which provide the therapeutic benefits of both NSAIDs and selective COX-2 inhibitors, while causing a much lower incidence of side-effects then are typically observed with such agents due to the protective effects imparted by modifying the pharmacologically active agents as described herein.

20 Claims, No Drawings

PROTECTED FORMS OF A COMBINATION OF PHARMACOLOGICALLY ACTIVE AGENTS AND USES THEREFOR

FIELD OF THE INVENTION

The present invention relates to novel conjugated forms of pharmacologically active agents, and methods for the preparation and use thereof In a particular aspect of the invention, methods are provided for treating pathological conditions with a protected form of a combination of pharmacologically active agents, thereby reducing the occurrence of side-effects caused thereby.

BACKGROUND OF THE INVENTION

Despite the advent of modem pharmaceutical technology, many drugs still possess untoward toxicities which often limit the therapeutic potential thereof For example, although non-steroid anti-inflammatory drugs (NSAIDs) are a class of compounds which are widely used for the treatment of inflammation, pain and fever, NSAIDs (e.g., naproxen, aspirin, ibuprofen and ketoprofen) can cause gastrointestinal ulcers, a side-effect that remains the major limitation to the use of NSAIDs (see, for example, J. L. Wallace, in Gastroenterol. 112:1000–1016 (1997); A. H. Soll et al., in Ann Intern Med. 114:307–319 (1991); and J. Bjarason et al., in Gastroenterol. 104:1832–1847 (1993)).

There are two major ulcerogenic effects of NSAIDs: (1) topical irritant effects on the epithelium of the gastrointestinal tract and (2) suppression of gastrointestinal prostaglandin synthesis. In recent years, numerous strategies have been attempted to design and develop new NSAIDs that reduce the damage to the gastrointestinal tract. These efforts, however, have largely been unsuccessful. For example, enteric coating or slow-release formulations designed to reduce the topical irritant properties of NSAIDs have been shown to be ineffective in terms of reducing the incidence of clinically significant side effects, including perforation and bleeding (see, for example, D. Y. Graham et al., in Clin. Pharmacol. Ther. 38:65–70 (1985); and J. L. Carson, et al., in Arch. Intern. Med., 147:1054–1059 (1987)).

It is well recognized that aspirin and other NSAIDs exert their pharmacological effects through the non-selective inhibition of cyclooxygenase (COX) enzymes, thereby blocking prostaglandin synthesis (see, for example, J. R. Van in Nature, 231:232–235 (1971)). There are two types of COX enzymes, namely COX-1 and COX-2. COX-1 is expressed constitutively in many tissues, including the stomach, kidney, and platelets, whereas COX-2 is expressed only at the site of inflammation (see, for example, S. Kargan et al. in Gastroenterol., 111:445–454 (1996)). The prostagladins derived from COX-1 are responsible for many of the physiological effects, including maintenance of gastric mucosal integrity.

Many attempts have been made to develop NSAIDs that only inhibit COX-2, without impacting the activity of COX-1 (see, for example, J. A. Mitchell et al., in Proc. Natl. Acad. Sci. USA 90:11693–11697 (1993); and E. A. Meade et al., in J. Biol. Chem., 268:6610–6614 (1993)). There are several NSAIDs presently on the market (e.g., rofecoxib and celecoxib) that show marked selectivity for COX-2 (see, for example, E. A. Meade, supra.; K. Glaser et al., in Eur. J. Pharmacol. 281:107–111 (1995) and Kaplan-Machlis, B., and Klostermeyer, BS in Ann Pharmacother. 33:979–88, (1999)). These drugs appear to have reduced gastrointestinal toxicity relative to other NSAIDs on the market.

On the basis of encouraging clinical as well as experimental data, the development of highly selective COX-2 inhibitors appears to be a sound strategy to develop a new generation of anti-inflammatory drugs. However, the physiological functions of COX-1 and COX-2 are not always well defined. Thus, there is a possibility that prostagladins produced as a result of COX-1 expression may also contribute to inflammation, pain and fever. On the other hand, prostagladins produced by COX-2 have been shown to play important physiological functions, including the initiation and maintenance of labor and in the regulation of bone resorption (see, for example, D. M. Slater et al., in Am J. Obstet Gynecol., 172:77–82 (1995); and Y. Onoe et al., in J. Immunol. 156:758–764 (1996)), thus inhibition of this pathway may not always be beneficial. Considering these points, highly selective COX-2 inhibitors may produce additional side effects above and beyond those observed with standard NSAIDs, therefore such inhibitors may not be highly desirable.

Indeed, recent studies with first generation COX-2 inhibitors reveal that arthritic patients treated with rofecoxib had a five-fold higher risk of heart attack,compared to patients treated with naproxen (Wale St. Jrnl, 5/1/10). Thus, like aspirin, naproxen appears to exert cardioprotecture effects, while selective COX-2 inhibitors do not.

Accordingly, there is still a need in the art for modified forms of NSAIDs, and other pharmacologically active agents, e.g., selective COX-2 inhibitors, which cause a reduced incidence of side-effects, relative to the incidence of side-effects caused by such pharmacologically active agents in unmodified form.

BRIEF DESCRIPTION OF THE INVENTION

In accordance with the present invention, there are provided conjugates of a combination of pharmacologically active agents (e.g., NSAIDs and selective COX-2 inhibitors). Invention conjugates (e.g., NSAID-COX-2) provide a new class of pharmacologically active agents (e.g., anti-inflammatory agents) which provide the therapeutic benefits of both NSAIDs and selective COX-2 inhibitors, while causing a much lower incidence of side-effects than are typically observed with such agents due to the protective effects imparted by modifying the pharmacologically active agents as described herein.

There are a number of advantages of conjugates according to the invention (e.g., NSAID-COX-$2^i$), including:

(i) reduced topical irritant effects of NSAIDs and COX-2 inhibitors, and (ii) enhanced tissue delivery of both drugs as a result of a decrease in net charges on the molecule, particularly for acidic NSAIDs such as naproxen, aspirin, diclofenac and ibuprofen, thereby reducing the quantity of material which must be delivered to.

In accordance with the present invention, cleavage of the novel bio-cleavable conjugates described herein releases both components thereof as active pharmaceutical agents.

DETAILED DESCRIPTION OF THE INVENTION

In accordance with the present invention, there are provided compounds comprising a conjugate wherein a NSAID is covalently attached to a selective COX-2 inhibitor. Invention compounds have the structure:

X-L-Y wherein:

X=a non-steroidal anti-inflammatory drug (NSAID),

L=an optional linker/spacer, and

Y=a selective COX-2 inhibitor.

Invention compounds can be readily prepared in a variety of ways, e.g., by direct reaction of NSAIDs with COX-2 inhibitors, or by indirectly linking NSAIDs to COX-2 inhibitors employing a suitable linker/spacer.

The components of invention conjugates are directly or indirectly covalently attached employing a variety of linkages (including an optional linker), e.g., ester linkages, disulfide linkages, amide linkages, immine linkages, enamine linkages, ether linkages, thioether linkages, imide linkages, sulfate ester linkages, sulfonate ester linkages, sulfone linkages, sulfonamide linkages, phosphate ester linkages, carbonate linkages, O-glycosidic linkages, S-glycosidic linkages, and the like. Such linkages can be accomplished using standard synthetic techniques as are well known by those of skill in the art, either by direct reaction of the starting materials, or by incorporating a suitable functional group on the starting material, followed by coupling of the reactants.

When the phanrmacologically active agents contemplated for use herein contain suitable functionality thereon, e.g., hydroxy, amino, carboxy, and the like, invention conjugate can be prepared by direct linkage between the two agents. Alternatively, one or both of the pharmacologically active agents can be functionalized so as to facilitate linkage between the two agents. When present, linker/spacer L has one of the following structures:

-Z-W-,

-W-Z-, or

-W-Z-W- wherein:

Z is alkylene, substituted alkylene, cycloalkylene, substituted cycloalkylene, heterocyclic, substituted heterocyclic, oxyalkylene, substituted oxyalkylene, alkenylene, substituted alkenylene, arylene, substituted arylene, alkarylene, substituted alkarylene, aralkylene or substituted aralkylene, and W=ester, reverse ester, thioester, reverse thioester, amide, reverse amide, phosphate, phosphonate, sulfone, sulfonamide, immine or enamine.

As employed herein, "alkylene" refers to divalent hydrocarbyl radicals having 1 up to 20 carbon atoms, preferably 2–10 carbon atoms; and "substituted alkylene" comprises alkylene groups further bearing one or more substituents selected from hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, —C(O)H, acyl, oxyacyl, carboxyl, carbamate, sulfonyl, sulfonamide, sulfuryl, and the like.

As employed herein, "cycloalkylene" refers to cyclic ring-containig groups containing in the range of about 3 up to 8 carbon atoms, and "substituted cycloalkylene" refers to cycloalkylene groups further bearing one or more substituents as set forth above.

As employed herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As employed herein, "oxyalkylene" refers to the moiety -O-alkylene-, wherein alkylene is as defined above, and "substituted oxyalkylene" refers to oxyalkylene groups further bearing one or more substituents as set forth above.

As employed herein, "alkenylene" refers to divalent, straight or branched chain hydrocarbyl groups having at least one carbon-carbon double bond, and having in the range of about 2 up to 12 carbon atoms, and "substituted alkenylene" refers to alkenylene groups further bearing one or more substituents as set forth above.

As employed herein, "alkynylene" refers to divalent straight or branched chain hydrocarbyl groups having at least one carbon-carbon triple bond, and having in the range of about 2 up to 12 carbon atoms, and "substituted alkynylene" refers to alkynylene groups further bearing one or more substituents as set forth above.

As employed herein, "arylene" refers to divalent aromatic groups having in the range of 6 up to 14 carbon atoms and "substituted arylene" refers to arylene groups further bearing one or more substituents as set forth above.

As employed herein, "alkylarylene" refers to alkyl-substituted arylene groups and "substituted alkylarylene" refers to alkylarylene groups further bearing one or more substituents as set forth above.

As employed herein, "arylalkylene" refers to aryl-substituted alkylene groups and "substituted arylalkylene" refers to arylalkylene groups further bearing one or more substituents as set forth above.

As employed herein, "arylalkenylene" refers to aryl-substituted alkenylene groups and "substituted arylalkenylene" refers to arylalkenylene groups further bearing one or more substituents as set forth above.

As employed herein, "arylalkynylene" refers to aryl-substituted alkynylene groups and "substituted arylalkynylene" refers to arylalkynylene groups further bearing one or more substituents as set forth above.

Diseases and conditions contemplated for treatment in accordance with the present invention include inflammatory and infectious diseases, such as, for example, septic shock, hemorrhagic shock, anaphylactic shock, toxic shock syndrome, ischemia, cerebral ischemia, administration of cytokines, overexpression of cytokines, ulcers, inflammatory bowel disease (e.g., ulcerative colitis or Crohn's disease), diabetes, arthritis, asthma, Alzheimer's disease, Parkinson's disease, multiple sclerosis, cirrhosis, allograft rejection, encephalomyelitis, meningitis, pancreatitis, peritonitis, vasculitis, lymphocytic choriomeningitis, glomerulonephritis, uveitis, ileitis, inflammation (e.g., liver inflammation, renal inflammation, and the like), burn, infection (including bacterial, viral, fungal and parasitic infections), hemodialysis, chronic fatigue syndrome, stroke, cancers (e.g., breast, melanoma, carcinoma, and the like), cardiopulmonary bypass, ischemic/reperfusion injury, gastritis, adult respiratory distress syndrome, cachexia, myocarditis, autoimmune disorders, eczema, psoriasis, heart failure, heart disease, atherosclerosis, dermatitis, urticaria, systemic lupus erythematosus, AIDA, AIDS dementia, chronic neurodegenerative disease, chronic pain, priapism, cystic fibrosis, amyotrophic lateral sclerosis, schizophrenia, depression, premenstrual syndrome, anxiety, addiction, migraine, Huntington's disease, epilepsy, neurodegenerative disorders, gastrointestinal motility disorders, obesity, hyperphagia, solid tumors (e.g., neuroblastoma), malaria, hematologic cancers, myelofibrosis, lung injury, graft-versus-host disease, head injury, CNS trauma, hepatitis, renal failure, liver disease (e.g., chronic hepatitis C), drug-induced lung injury (e.g., paraquat), myasthenia gravis (MG), ophthalmic diseases, post-angioplasty, restenosis, angina, coronary artery disease, and the like.

NSAIDs contemplated for modification in accordance with the present invention include acetaminophen (Tylenol, Datril, etc.), aspirin, ibuprofen (Motrin, Advil, Rufen, others), choline magnesium salicylate (Triasate), choline salicylate (Anthropan), diclofenac (voltaren, cataflam), diflunisal (dolobid), etodolac (lodine), fenoprofen calcium (nalfon), flurbiprofen (ansaid), indomethacin (indocin, indometh, others), ketoprofen (orudis, oruvail), carprofen, indoprofen, ketorolac tromethamine (toradol), magnesium salicylate (Doan's, magan, mobidin, others), meclofenamate sodium (meclomen), mefenamic acid (relafan), oxaprozin (daypro), piroxicam (feldene), sodium salicylate, sulindac (clinoril), tolnetin (tolectin), meloxicam, nabumetone, naproxen, lomoxicam, nimesulide, indoprofen, remifenzone, salsalate, tiaprofenic acid, flosulide, and the like. Presently preferred NSAIDs employed in the practice of the invention include naproxen, aspirin, ibuprofen, flurbiprofen, indomethacin, ketoprofen, carprofen, and the like.

Selective COX-2 inhibitors contemplated for modification in accordance with the present invention include celecoxib, rofecoxib, valdecoxib, and the like, as well as analogs, homologs and derivatives thereof.

In accordance with another embodiment of the present invention, there are provided methods for the preparation of protected forms of pharmacologically active agents, said method comprising covalently attaching two defined pharmacologically active agents to one another. The resulting conjugate provides a latent form of each of the pharmacologically active agents, releasing the biological activity thereof only when the conjugate is cleaved (e.g., by an esterase, amidase or other suitable enzyme).

As readily recognized by those of skill in the art, invention conjugates can be prepared in a variety of ways. See, for example, Scheme 1, wherein a NSAID (1) bearing a carboxylic moiety can be reacted with a hydroxy substituted COX-2 inhibitor (2) under conditions suitable to produce invention conjugate (3).

SCHEME 1

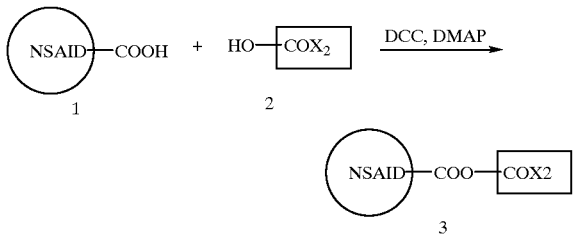

Employing this general reaction scheme, invention conjugates can be prepared from a wide variety of pharmacologically active agents. See, for example, Examples 1–13 provided herein.

In accordance with yet another embodiment of the present invention, there are provided methods for reducing the side effects induced by administration of NSAIDs to a subject, said method comprising covalently attaching a selective COX-2 inhibitor to said NSAID prior to administration to said subject.

In accordance with a further embodiment of the present invention, there are provided methods for reducing the side effects induced by administration of selective COX-2 inhibitors to a subject, said method comprising covalently attaching a NSAID to said selective COX-2 inhibitor prior to administration to said subject.

In accordance with still another embodiment of the present invention, there are provided methods for enhancing the effectiveness of NSAIDs, said method comprising covalently attaching a selective COX-2 inhibitor to said NSAID.

In accordance with yet another embodiment of the present invention, there are provided methods for enhancing the effectiveness of selective COX-2 inhibitors, said method comprising covalently attaching a NSAID to said selective COX-2 inhibitor.

In accordance with a still further embodiment of the present invention, there are provided improved methods for the administration of NSAIDs and/or selective COX-2 inhibitors to a subject for the treatment of a pathological condition, the improvement comprising covalently attaching said NSAID to said selective COX-2 inhibitor prior to administration thereof to said subject.

Those of skill in the art recognize that the conjugates described herein can be delivered in a variety of ways, such as, for example, orally, intravenously, subcutaneously, parenterally, rectally, by inhalation, and the like.

Depending on the mode of delivery employed, the conjugates contemplated for use herein can be delivered in a variety of pharmaceutically acceptable forms. For example, the conjugate can be delivered in the form of a solid, solution, emulsion, dispersion, micelle, liposome, and the like.

Thus, in accordance with still another embodiment of the present invention, there are provided physiologically active composition(s) comprising invention conjugates in a suitable vehicle rendering said conjugates amenable to oral delivery, transdermal delivery, intravenous delivery, intramuscular delivery, topical delivery, nasal delivery, and the like.

Pharmaceutical compositions of the present invention can be used in the form of a solid, a solution, an emulsion, a dispersion, a micelle, a liposome, and the like, wherein the resulting composition contains one or more of the compounds of the present invention, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention conjugate is included in the pharmaceutical composition in an amount sufficient to produce the desired effect upon the process or disease condition.

Pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing the active ingredient in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Conjugates contemplated for use in the practice of the present invention may also be administered in the form of suppositories for rectal administration of the drug. These compositions may be prepared by mixing the drug with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

In general, the dosage of invention conjugate employed as described herein falls in the range of about 0.01 mmoles/kg body weight of the subject/hour up to about 0.5 mmoles/kg/hr. Typical daily doses, in general, lie within the range of from about 10 µg up to about 100 mg per kg body weight, and, preferably within the range of from 50 µg to 10 mg per kg body weight and can be administered up to four times daily. The daily IV dose lies within the range of from about 1 µg to about 100 mg per kg body weight, and, preferably, within the range of from 10 µg to 10 mg per kg body weight.

In accordance with yet another embodiment of the present invention, there are provided improved methods for the treatment of a subject suffering from a pathological condition by administration thereto of a NSAID and/or a selective COX-2 inhibitor, the improvement comprising covalently attaching said NSAID to said selective COX-2 inhibitor prior to administration thereof to said subject.

Thus, invention method for the treatment of a subject afflicted with a pathological condition comprises administering to a subject an effective amount of a modified pharmacologically active agent, wherein said pharmacologically active agent is a NSAID or a selective COX-2 inhibitor, and is effective for treatment of said condition, and wherein said pharmacologically active agent has been modified by the covalent attachment thereto of a NSAID or a selective COX-2 inhibitor.

The invention will now be described in greater detail by reference to the following non-limiting examples.

EXAMPLE 1

General procedure for the preparation of conjugate compound 3 (Scheme 1). To a stirring solution of NSAID compound (1) (1 eq), COX-2 inhibitor (2) (1 eq) and dimethylaminopyridine (DMAP) (0.2 eq) in anhydrous THF is added 1,3-dicyclohexylcarbodiimide (DCC) (1 eq) at 0° C. The resulting solution is stirred at room temperature for several hours. The reaction solution is filtered and the solvent is evaporated. The residue is partially dissolved in ethyl acetate and the solid is filtered off and the solution is washed with 0.5 N HCl, saturated sodium bicarbonate solution and brine. After the solvent is evaporated, the compound is purified either by flash chromatography or crystallization to give compound 3.

EXAMPLE 2

The synthesis described in this and the following example is illustrated in Scheme 2:

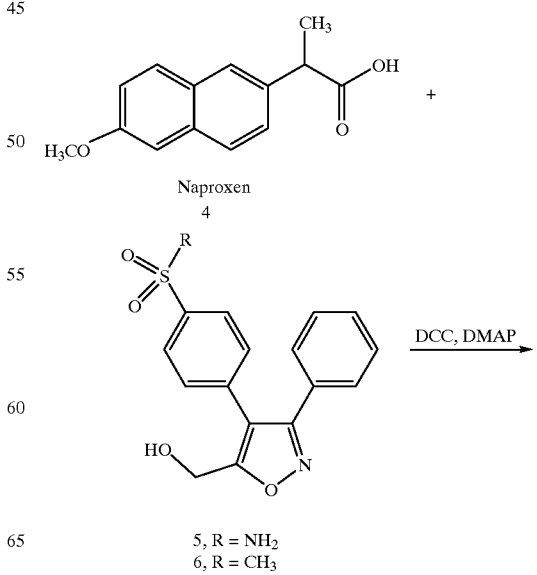

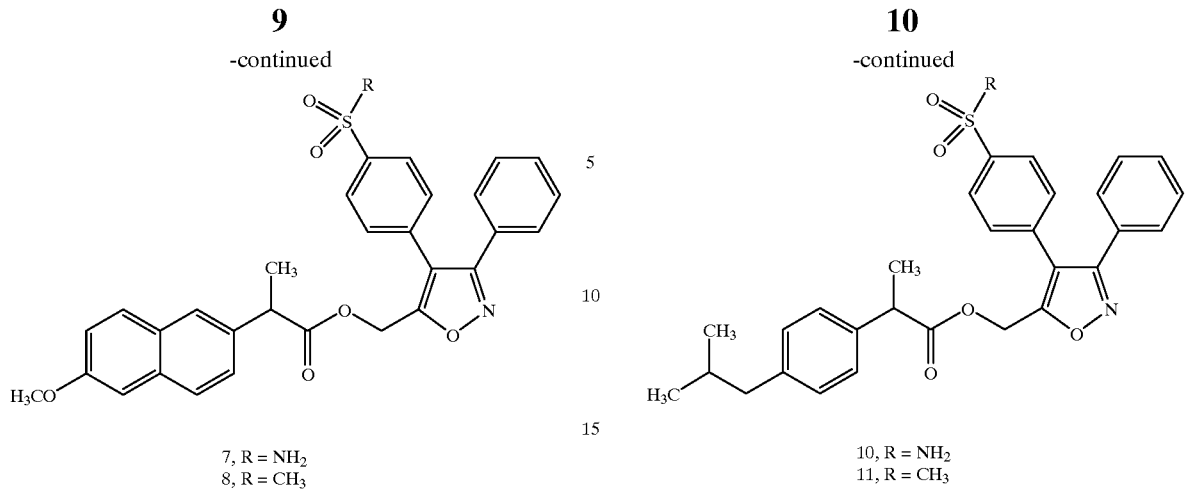

7, R = NH$_2$
8, R = CH$_3$

10, R = NH$_2$
11, R = CH$_3$

Compound 7 (Scheme 2). Compound 7 is prepared as described in the general procedure above for compound 3 from naproxen (2.30 g, 10 mmol), compound 5 (3.30 g, 10 mmol), DMAP (0.24 g, 2 mmol) and DCC (2.06 g, 10 mmol). The compound is purified by column chromatography on a silica gel column to give compound 7 with a yield from 50% to 80%.

EXAMPLE 3

Compound 8 (Scheme 2). Compound 8 is prepared as described in the general procedure above for compound 3 from naproxen (2.30 g, 10 mmol), compound 6 (3.29 g, 10 mmol), DMAP (0.24 g, 2 mmol) and DCC (2.06 g, 10 mmol). The compound is purified by column chromatography on a silica gel column to give compound 8 with a yield from 50% to 80%.

EXAMPLE 4

The synthesis described in this and the following example is illustrated in Scheme 3:

Compound 10 (Scheme 3). Compound 10 is prepared as described in the general procedure above for compound 3 from ibuprofen (2.06 g, 10 mmol), compound 5 (3.30 g, 10 mmol), DMAP (0.24 g, 2 mmol) and DCC (2.06 g, 10 mmol). The compound is purified by column chromatography on a silica gel column to give compound 10 with a yield from 50% to 80%.

EXAMPLE 5

Compound 11 (Scheme 3). Compound 11 is prepared as described in the general procedure above for compound 3 from ibuprofen (2.06 g, 10 mmol), compound 6 (3.29 g, 10 mmol), DMAP (0.24 g, 2 mmol) and DCC (2.06 g, 10 mmol). The compound is purified by column chromatography on a silica gel column to give compound 11 with a yield from 50% to 80%.

EXAMPLE 6

The synthesis described in this and the following example is illustrated in Scheme 4:

SCHEME 3

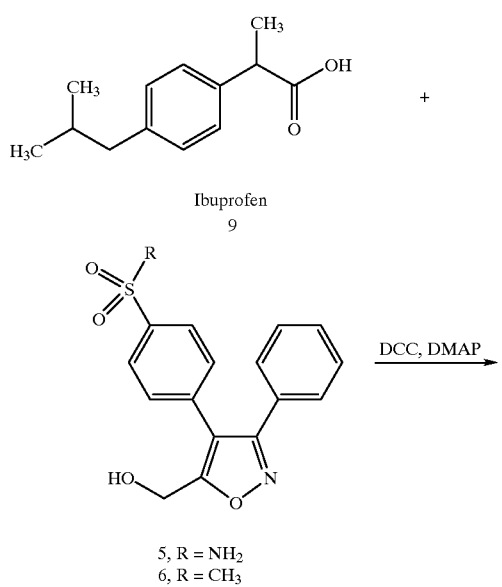

Ibuprofen
9

5, R = NH$_2$
6, R = CH$_3$

SCHEME 4

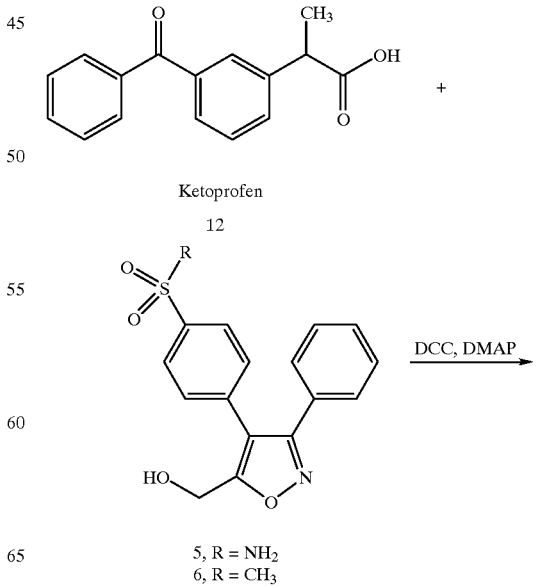

Ketoprofen
12

5, R = NH$_2$
6, R = CH$_3$

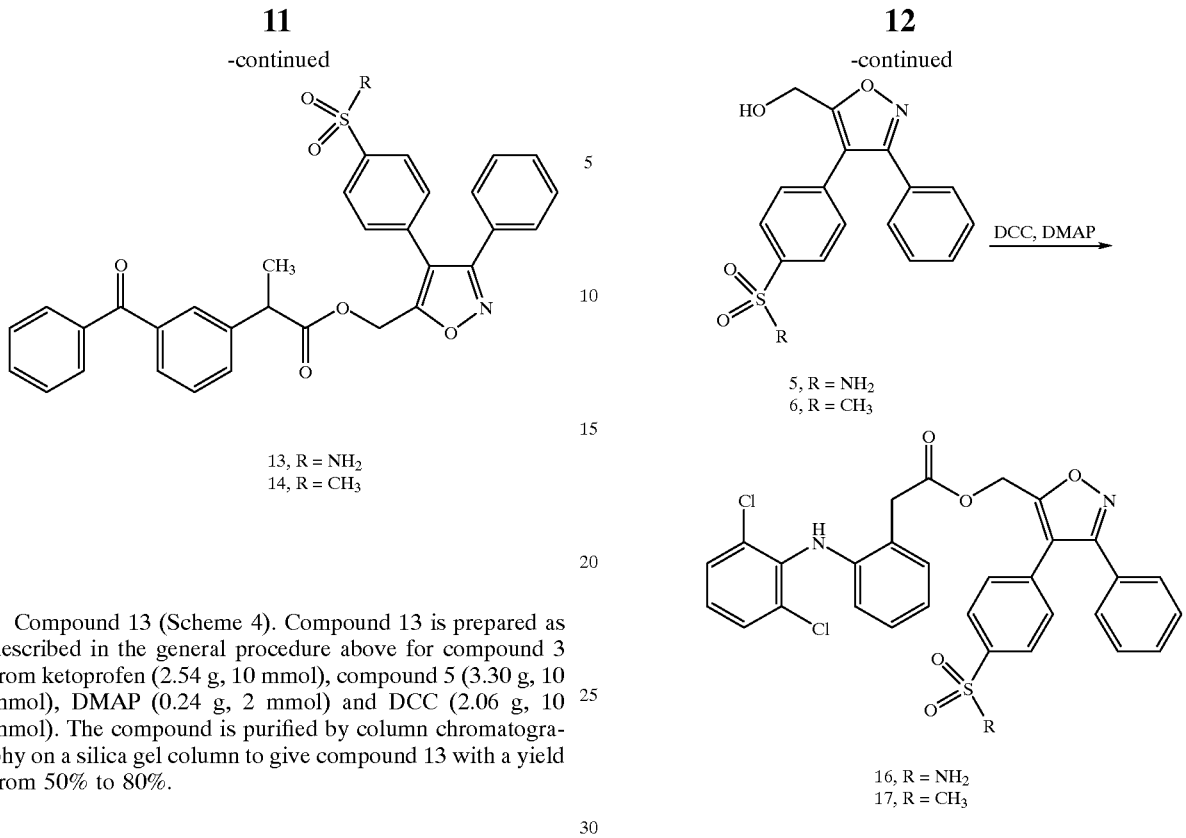

13, R = NH₂
14, R = CH₃

5, R = NH₂
6, R = CH₃

16, R = NH₂
17, R = CH₃

Compound 13 (Scheme 4). Compound 13 is prepared as described in the general procedure above for compound 3 from ketoprofen (2.54 g, 10 mmol), compound 5 (3.30 g, 10 mmol), DMAP (0.24 g, 2 mmol) and DCC (2.06 g, 10 mmol). The compound is purified by column chromatography on a silica gel column to give compound 13 with a yield from 50% to 80%.

EXAMPLE 7

Compound 14 (Scheme 4). Compound 14 is prepared as described in the general procedure above for compound 3 from ketoprofen (2.54 g, 10 mmol), compound 6 (3.29 g, 10 mmol), DMAP (0.24 g, 2 mmol) and DCC (2.06 g, 10 mmol). The compound is purified by column chromatography on a silica gel column to give compound 14 with a yield from 50% to 80%.

EXAMPLE 8

The synthesis described in this and the following example is illustrated in Scheme 5:

SCHEME 5

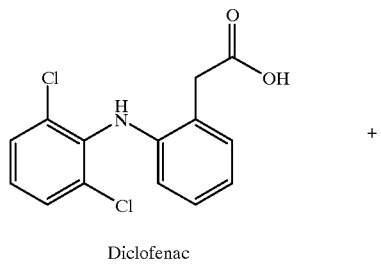

Diclofenac
15

+

Compound 16 (Scheme 5). Compound 16 is prepared as described in the general procedure above for compound 3 from diclofenac (2.96 g, 10 mmol), compound 5 (3.30 g, 10 mmol), DMAP (0.24 g, 2 mmol) and DCC (2.06 g, 10 mmol). The compound is purified by column chromatography on a silica gel column to give compound 16 with a yield from 50% to 80%.

EXAMPLE 9

Compound 17 (Scheme 5). Compound 17 is prepared as described in the general procedure above for compound 3 from diclofenac (2.96 g, 10 mmol), compound 6 (3.29 g, 10 mmol), DMAP (0.24 g, 2 mmol) and DCC (2.06 g, 10 mmol). The compound is purified by column chromatography on a silica gel column to give compound 17 with a yield from 50% to 80%.

EXAMPLE 10

The synthesis described in this and the following example is illustrated in Scheme 6:

SCHEME 6

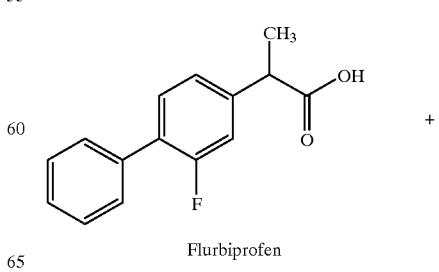

Flurbiprofen
18

+

13

-continued

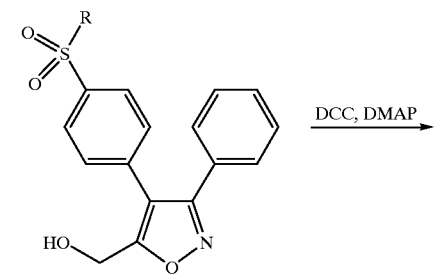

5, R = NH₂
6, R = CH₃

DCC, DMAP →

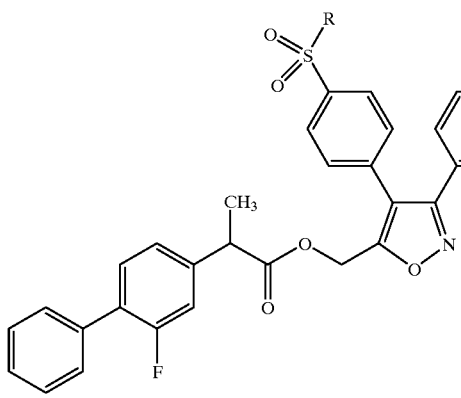

19, R = NH₂
20, R = CH₃

Compound 19 (Scheme 6). Compound 19 is prepared as described in the general procedure above for compound 3 from flurbiprofen (2.44 g, 10 mmol), compound 5 (3.3 g, 10 mmol), DMAP (0.24 g, 2 mmol) and DCC (2.06 g, 10 mmol). The compound is purified by column chromatography on a silica gel column to give compound 19 with a yield from 50% to 80%.

EXAMPLE 11

Compound 20 (Scheme 6). Compound 20 is prepared as described in the general procedure above for compound 3 from flurbiprofen (2.44 g, 10 mmol), compound 6 (3.29 g, 10 mmol), DMAP (0.24 g, 2 mmol) and DCC (2.06 g, 10 mmol). The compound is purified by column chromatography on a silica gel column to give compound 20 with a yield from 50% to 80%.

EXAMPLE 12

The synthesis described in this and the following example is illustrated in Scheme 7:

14

SCHEME 7

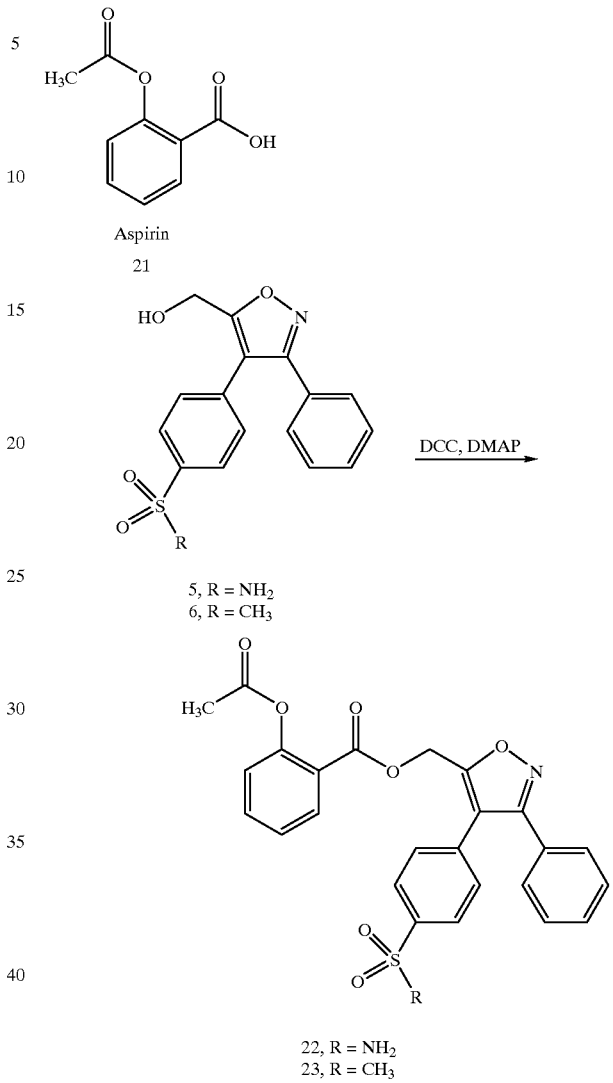

Aspirin
21

5, R = NH₂
6, R = CH₃

DCC, DMAP →

22, R = NH₂
23, R = CH₃

Compound 22 (Scheme 7). Compound 22 is prepared as described in the general procedure above for compound 3 from aspirin (1.80 g, 10 mmol), compound 5 (3.30 g, 10 mmol), DMAP (0.24 g, 2 mmol) and DCC (2.06 g, 10 mmol). The compound is purified by column chromatography on a silica gel column to give compound 22 with a yield from 50% to 80%.

EXAMPLE 13

Compound 23 (Scheme 7). Compound 23 is prepared as described in the general procedure above for compound 3 from aspirin (1.80 g, 10 mmol), compound 6 (3.29 g, 10 mmol), DMAP (0.24 g, 2 mmol) and DCC (2.06 g, 10 mmol). The compound is purified by column chromatography on a silica gel column to give compound 23 with a yield from 50% to 80%.

EXAMPLE 14

Evaluation of the Effects of the Conjugate of Naproxen and Selective COX-2 Inhibitor of the Invention on Acute Gastric Mucosal Injury Wistar rats (200–250 grams, male) are fasted overnight but allowed free access to water. Ten rats in each group are given naproxen, selective COX-2 inhibitor or an invention conjugate thereof orally at doses of 10, 20 or 50 mg/kg. The rats are sacrificed five hours later and the visible gastric damage is assessed by examining under microscope and by histological evaluation.

For all three doses used, invention conjugate produces the least visible gastric lesions, compared to the lesions induced by either naproxen or COX-2 inhibitor alone. This is attributed to the stability and inactivity of the invention conjugate in the stomach, thereby reducing local irritation and damage.

EXAMPLE 15

Evaluation on the Anti-inflammatory Effects of the Conjugate of Naproxen and Selective COX-2 Inhibitor of the Invention Wistar rats (male, 200–250 grams) are fasted overnight but allowed to free access to drinking water. Naproxen, selective COX-2 inhibitor or an invention conjugate thereof is given orally at a dose of 1, 10 or 30 mg/kg (6 animals per group). After one hour, the rats are anesthetized and 0.1 ml of lambda carrageenan (0.1% solution) is injected into the right hind foot pad. The volume of the pad is measured by hydropletysmometry every hour for the next five hours.

The control group (given saline orally) shows a time-dependent increase in the volume of the footpad to near 0.7–1.0 ml at the five-hour time point. On the other hand, all three treated groups reveal a dose-dependent reduction of the volume of the footpad. This suggests that the invention conjugate is as effective as either naproxen or COX-2 inhibitor administered alone for alleviation of acute inflammation induced by carrageenan, implying that upon in vivo absorption, naproxen and COX-2 inhibitor are released from the invention conjugate in the circulation and are fully active to exert their anti-inflammatory effects.

EXAMPLE 16

Evaluation of the Effects of the Conjugate of Naproxen and Selective COX-2 Inhibitor on Prostaglandin Synthesis Wistar rats (male, 200–250 grams) are fasted overnight but allowed free access to drinking water. The rats are anesthetized and their backs are shaved. After an incision to the back, a sponge (2.5×1×0.5 cm) soaked with 2 ml of 0.5% carrageenan is implanted. Five hours later, the rats (6 animals in each group) are given orally naproxen, selective COX-2 inhibitor or an invention conjugate thereof at a dose of 30 mg/kg or vehicle control. One hour later, the rats are sacrificed and the sponge is carefully removed. The exudate is recovered from the sponge and the prostaglandin E2 level in the exudate is measured by enzyme-linked immunosorbent assay.

In the control group (saline orally), the prostaglandin levels in the recovered exudates increase with time from 300 pg/ml to over 3000 pg/ml. In contrast, all three treated groups show substantial decreases in prostaglandin levels. The increase in prostaglandin levels is indicative of inflammatory reaction. The results suggest that the invention conjugate is cleaved in vivo, thereby releasing both naproxen and COX-2 inhibitor and exerting anti-inflammatory activities.

EXAMPLE 17

The Effects of the Conjugate of Naproxen and Selective COX-2 Inhibitor on Chronic Hindlimb Inflammation in the Rat Adjuvant Arthritis Model Lewis male rats (175–250 grams) are injected intradermally in the footpad with M. tuberculosis powder suspended in mineral oil at 5 mg/ml. Rats are dosed daily by oral gavage with 5 ml/kg of naproxen or selective COX-2 inhibitor at 1 and 10 mg/kg or equimolar doses of the new conjugate on days 5–8 and 11–14. Progressive swelling of the uninjected paw and ankle point between days 11 and 15 are measured by plethysmometry.

In this rat adjuvant arthritis study, at day 15 the volume of the footpad in the control group (saline orally) increases by 1.5 to 2.0 ml over that of the untreated normal rats. However, all three treated groups show great reduction in the volume of the footpad at day 15, suggesting that all three agents, naproxen alone, COX-2 inhibitor alone and invention conjugate are equally effective as anti-arthritic treatment agents. This example demonstrates that the invention conjugate is readily converted into the active components of naproxen and COX-2 inhibitor in vivo in the circulation upon absorption in the intestines.

While the invention has been described in detail with reference to certain preferred embodiments thereof, it will be understood that modifications and variations are within the spirit and scope of that which is described and claimed.

That which is claimed is:

1. A compound having the structure:

X-L-Y wherein:
    X=a non-steroidal anti-inflammatory drug (NSAID),
    L=an optional linker/spacer, and
    Y=a selective COX-2 inhibitor.

2. A compound according to claim 1 wherein said NSAID is acetaminophen, aspirin, ibuprofen, choline magnesium salicylate, choline salicylate, diclofenac, diflunisal, etodolac, fenprofen calcium, flurobiprofen, indomethacin, ketoprofen, carprofen, indoprofen, ketorolac tromethamine, magnesium salicylate, meclofenamate sodium, mefenamic acid, oxaprozin, piroxicam, sodium salicylate, sulindac, tolmetin, meloxicam, nabumetone, naproxen, lornoxicam, nimesulide, indoprofen, remifenzone, salsalate, tiaprofenic acid, or flosulide.

3. A compound according to claim 2 wherein said NSAID is naproxen, aspirin, ibuprofen, flurbiprofen, indomethacin, ketoprofen, or carprofen.

4. A compound according to claim 1 wherein said selective COX-2 inhibitor is celecoxib, rofecoxib, valdecoxib, or derivatives.

5. A compound according to claim 4 wherein said selective COX-2 inhibitor is valdecoxib or derivatives thereof.

6. A compound according to claim 1 wherein L has the structure:

-Z-W-, -W-Z-, or -W-Z-W-, wherein:
    Z is alkylene, substituted alkylene, cycloalkylene, substituted cycloalkylene, heterocyclic, substituted heterocyclic, oxyalkylene, substituted oxyalkylene, alkenylene, substituted alkenylene, arylene, substituted arylene, alkarylene, substituted alkarylene, aralkylene or substituted aralkylene, and
    W is ester, reverse ester, thioester, reverse thioester, amide, reverse amide, phosphate, phosphonate, sulfone, salfonamide, immine or enamine.

7. A formulation comprising a compound according to claim 1 in a pharmaceutically acceptable carrier therefor.

8. A formulation according to claim 7 wherein said pharmaceutically acceptable carrier is a solid, solution, emulsion, dispersion, micelle or liposome.

9. A formulation according to claim 7 wherein said pharmaceutically acceptable carrier further comprises an enteric coating.

10. In the administration of a non-steroidal anti-inflammatory drug (NSAID) and/or a selective COX-2 inhibitor to a subject for the treatment of a pathological condition, the improvement comprising covalently attaching said NSAID to said selective COX-2 inhibitor prior to administration thereof to said subject.

11. In the treatment of a subject suffering from a pathological condition by administration thereto of a non-steroidal anti-inflammatory drug (NSAID) and/or a selective COX-2 inhibitor, the improvement comprising covalently attaching said NSAID to said selective COX-2 inhibitor prior to administration thereof to said subject.

12. A method for the treatment of a subject afflicted with a pathological condition, said method comprising administering to said subject an effective amount of a non-steroidal anti-inflammatory drug (NSAID), wherein said NSAID is effective for treatment of said condition, and wherein said NSAID has been modified by the covalent attachment thereto of a selective COX-2 inhibitor.

13. A method for the preparation of a protected form of a non-steroidal anti-inflammatory drug (NSAID), said method comprising covalently attaching a selective COX-2 inhibitor to said NSAID.

14. A method for reducing the side effects induced by administration of a non-steroidal anti-inflammatory drug (NSAID) to a subject, said method comprising covalently attaching a selective COX-2 inhibitor to said NSAID prior to administration to said subject.

15. A method for enhancing the effectiveness of a non-steroidal anti-inflammatory drug (NSAID), said method comprising covalently attaching a selective COX-2 inhibitor to said NSAID.

16. A method for the treatment of a subject afflicted with a pathological condition, said method comprising administering to said subject an effective amount of a selective COX-2 inhibitor, wherein said selective COX-2 inhibitor is effective for treatment of said condition, and wherein said selective COX-2 inhibitor has been modified by the covalent attachment thereto of a non-steroidal anti-inflammatory drug (NSAID).

17. A method for the preparation of a protected form of a selective COX-2 inhibitor, said method comprising covalently attaching a non-steroidal anti-inflammatory drug (NSAID) to said selective COX-2 inhibitor.

18. A method for reducing the side effects induced by administration of a selective COX-2 inhibitor to a subject, said method comprising covalently attaching a non-steroidal anti-inflammatory drug (NSAID) to said selective COX-2 inhibitor prior to administration to said subject.

19. A method for enhancing the effectiveness of a selective COX-2 inhibitor, said method comprising covalently attaching a non-steroidal anti-inflammatory drug (NSAID) to said selective COX-2 inhibitor.

20. A method for the prevention or treatment of an inflammatory or infectious disease in a subject in need thereof, said method comprising administering to said subject an amount of the compound of claim 1 effective to alleviate said condition.

* * * * *